United States Patent [19]

Kitano et al.

[11] Patent Number: 4,824,596
[45] Date of Patent: Apr. 25, 1989

[54] 2-(TRANS-4-ALKYLCYCLOHEXYL)-5-ALKOXYPYRIMIDINES

[75] Inventors: Kisei Kitano; Yasuyuki Goto, both of Yokohama, Japan

[73] Assignee: Chisso Corporation, Japan

[21] Appl. No.: 71,380

[22] Filed: Jul. 9, 1987

[30] Foreign Application Priority Data

Jul. 14, 1986 [JP] Japan ................ 61-165443

[51] Int. Cl.⁴ .................. C09K 19/34; C07D 239/02; G02F 1/13
[52] U.S. Cl. ............. 252/299.61; 252/299.5; 350/350 R; 544/298
[58] Field of Search .......... 252/299.61, 299.5, 299.01; 350/350 R; 544/298

[56] References Cited

U.S. PATENT DOCUMENTS

| | | | |
|---|---|---|---|
| 4,462,923 | 7/1984 | Boller et al. | 252/299.63 |
| 4,621,901 | 11/1986 | Petrzilka et al. | 252/299.61 |
| 4,632,515 | 12/1986 | Gray et al. | 252/299.61 |
| 4,694,098 | 9/1987 | Hirai et al. | 252/299.61 |
| 4,752,414 | 6/1988 | Eidenschime et al. | 252/299.61 |

FOREIGN PATENT DOCUMENTS

| | | | |
|---|---|---|---|
| 56501 | 7/1982 | European Pat. Off. | 252/299.61 |
| 0152697 | 8/1985 | European Pat. Off. | 252/299.61 |
| 3404116 | 8/1985 | Fed. Rep. of Germany | 252/299.61 |
| 3515373 | 11/1986 | Fed. Rep. of Germany | 252/299.61 |
| 60-51778 | 3/1985 | Japan | 252/299.61 |
| 60-193969 | 10/1985 | Japan | 252/299.61 |
| 2092169 | 8/1982 | United Kingdom | 252/299.61 |

Primary Examiner—Teddy S. Gron
Attorney, Agent, or Firm—Leydig, Voit & Mayer

[57] ABSTRACT

Novel compounds which, when used as a component of nematic liquid crystal compositions, can improve the characteristics of Δn and viscosity of the resulting liquid crystal compositions and also does not greatly adversely affect other characteristics thereof, and a liquid crystal composition containing such a compound are provided, which compound is expressed by the formula

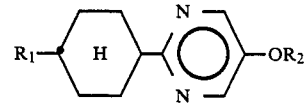

wherein $R_1$ and $R_2$ each independently represent an alkyl group of 1 to 12 carbon atoms.

10 Claims, No Drawings

2-(TRANS-4-ALKYLCYCLOHEXYL)-5-ALKOXYPYRIMIDINES

BACKGROUND OF THE INVENTION

This invention relates to a novel liquid crystalline compound and a liquid crystal composition containing the same.

Liquid crystal substances and their compositions have been used for various display devices, making use of the dielectric anisotropy (abbreviated to Δε) and optical anisotropy (abbreviated to Δn) in the liquid crystalline phases thereof.

Liquid crystal display modes include various modes such as electrically controlled birefringence mode (ECB mode), twisted nematic mode (TN mode), supertwisted birefringence effect mode(SBE mode), dynamic scattering mode (DS mode), guest-host mode, etc., corresponding on the applied electrooptical effect.

Liquid crystal materials used for display devices are required to have various characteristics depending on the display mode and also on the purpose of use of the devices. Those characteristics required are, for example, a broad mesomorphic range, a low viscosity, a large positive Δε value or a negative Δε value, and various characteristics of display devices (particularly threshold valtage thereof) which are less dependent on a temperature change over a broad temperature range.

At present, however, there is no single compound which is practical in the aspect of the temperature range of liquid crystal phases, and operating voltage and resonse properties of display devices. Thus, mixtures of several kinds of liquid crystal compounds or mixtures of several kinds of liquid crystal compounds with compounds having liquid crystal properties latently or non-liquid crystal substances have been practically used.

Further, in the case of TN type cells, as reported by G. Bauer in Mol. Cryst. Liq. Cryst. 63, 43 (1981), it is necessary to select the product of the Δn of liquid crystal materials filled in the cell and the thickness (d) μm of the cell to a definite value in order to prevent the occurrence of the interference fringes on the surface of the display cell which causes to spoil the appearance of the cell. In the use of liquid crystal display cells, the value of Δn×d has been selected to any one of 0.5, 1.0, 1.6 or 2.2.

Thus, for preparing a liquid crystal material having an optional Δn, a liquid crystalline compound having a small Δn and also having a good balanced of various other characteristics is required.

A group of known compounds which satisfy this object are 2-(trans-4-n-alkylcyclohexyl)-5-n-alkylpyrimidines disclosed in U.S. Pat. No. 4,462,923. However, compounds of this type exhibit no nematic liquid crystal phase, or exhibit a nematic phase through a monotropic phase transition or have only a smectic phase as a liquid crystal phase; thus they are poor in nematic properties.

Examples of such compounds are as follows:
2-(trans-4-pentylcyclohexyl)-5-heptylpyrimidine CS point 22° C., SI point 40.5° C.
2-(trans-4-propylcyclohexyl)-5-propylpyrimidine m.p. 25° C.
2-(trans-4-propylcyclohexyl)-5-butylpyrimidine m.p. 9° C.
2-(trans-4-pentylcyclohexyl)-5-propylpyrimidine m.p. 26° C.
2-(trans-4-pentylcyclohexyl)-5-butylpyrimidine m.p. 3.5° C., NI point −7° C. (monotropic)
2-(trans-4-pentylcyclohexyl)-5-pentylpyrimidine m.p. 17° C., NI point 10° C. (monotropic)
2-(trans-4-heptylcyclohexyl)-5-heptylpyrimidine CS point 19° C., SI point 45° C.

SUMMARY OF THE INVENTION

An object of the present invention is to provide compounds which, when used as a component of nematic liquid crystal compositions, can improve both characteristics of Δn and viscosity of the resulting liquid crystal compositions and also does not greatly adversely affect other characteristics thereof.

Another object of the present invention is to provide a nematic liquid crystal composition having a Δn value suitable for realizing the above-mentioned Δn×d.

The present invention in a first aspect resides in a 2-(trans-4-alkylcyclohexyl)-5-alkoxypyrimidine compound expressed by the formula (I)

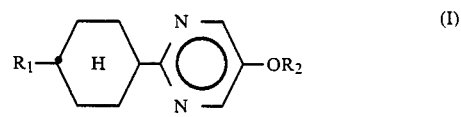 (I)

wherein $R_1$ and $R_2$ each independently represent an alkyl group of 1 to 12 carbon atoms. The present invention in a second aspect resides in a liquid crystal composition comprising at least one liquid crystal compound and at least one pyrimidine compound expressed by the above formula (I).

DETAILED DESCRIPTION OF PREFERRED EMBODIMENTS

A preferred embodiment of the first invention is a pyrimidine compound expressed by the formula (I) wherein $R_1$ and $R_2$ each are a linear alkyl group of 1 to 7 carbon atoms. Among those compounds, a pyrimidine compound having both a lower alkyl group and a lower alkoxy group is more preferable because of its low viscosity and its nematic property. Though the compound having lower alkyl and alkoxy groups does not per se exhibit a nematic range, it does not lower the NI point of the nematic mixture thereof so much. Thus it is usable as a viscosity-reducing component in a nematic mixture.

A pyrimidine compound having a linear alkyl group of 5 to 7 carbon atoms as $R_1$ is also preferable because of its well balanced properties.

The preparation of a compound of the present invention will be described by way of the following reaction equations. The reactions of the respective steps are known, but they are novel in the aspect of an overall synthetic reaction for obtaining the compound expressed by the formula (I):

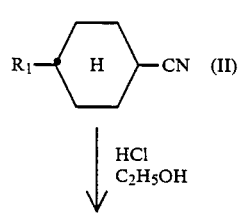

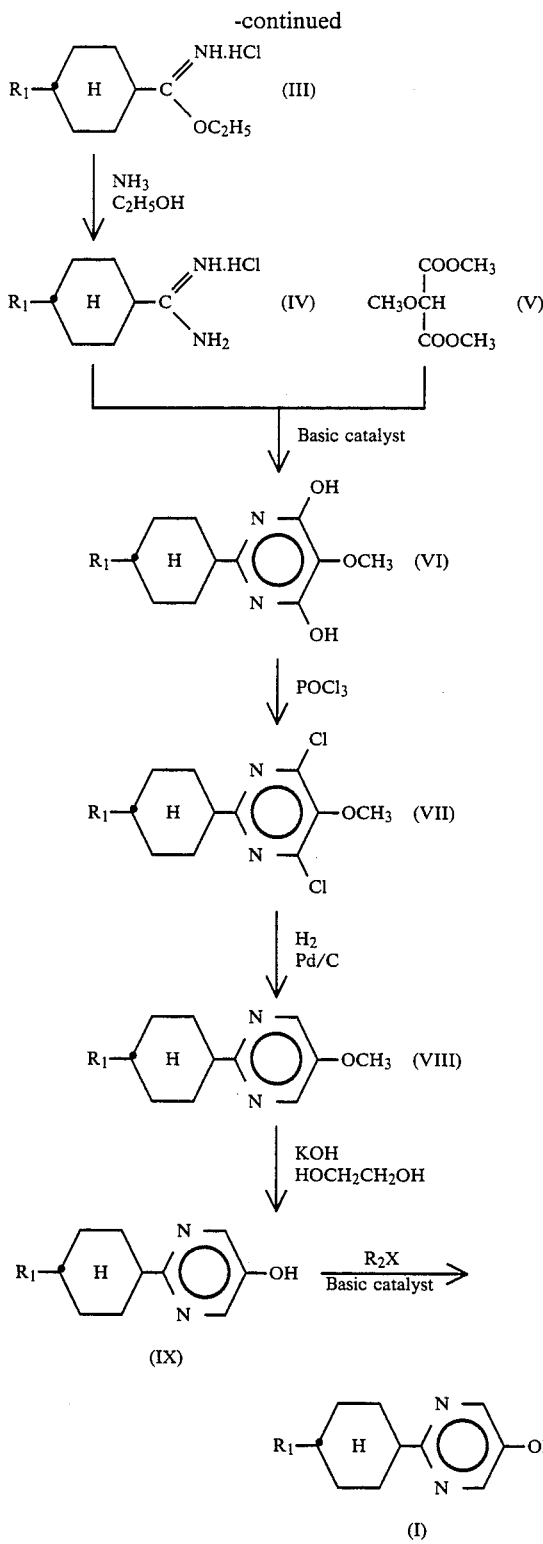

In the above equations, $R_1$ and $R_2$ each independently represent an alkyl group of 1 to 12 carbon atoms and X represents iodine or bromine.

Firstly, a trans-4-alkylcyclohexanecarbonitrile (II) is reacted with hydrogen chloride gas and alcohol to obtain an iminoether hydrochloride derivative (III) which is then reacted with ammonia gas in an alcohol solvent to obtain an amidine hydrochloride (IV). This compound (IV) is then subjected together with dimethyl methoxymalonate (V) to a condensation-cyclization reaction in the presence of a basic catalyst such as metal alcoholates, sodium hydroxide, 1,8-diazabicyclo[5.4.0]-7-undecene, etc. to obtain a 2-(trans-4-alkylcyclohexyl)-4,6-dihydroxy-5-methoxypyrimidine (VI), which is then chlorinated with phosphorus oxychloride to obtain a 2-(trans-4-alkylcyclohexyl)-4,6-dichloro-5-methoxypyrimidine (VII). The compound (VII) is then hydrogenated with palladium on carbon as catalyst to obtain a 2-(trans-4-alkylcyclohexyl)-5-mathoxypyrimidine (VIII). This compound (VIII) is one of the compounds of the present invention. As to compounds (I), those having an $R_2$ other than methyl group may be prepared as follows using the compound (VIII) as a raw material:

The compound (VIII) is further reacted in an ethylene glycol solvent in the presence of potassium hydroxide to obtain a 2-(trans-4-alkylcyclohexyl)-5-hydroxypyrimidine (IX) which is then finally reacted with an alkyl halide in the presence of a basic catalyst such as metal alcoholates, sodium hydroxide, 1,8-diazabicyclo[5.4.0]-7-undecene, etc. to obtain a 2-(trans-4-alkylcyclohexyl)-5-alkoxypyrimidine (I).

The compounds of the present invention are liquid crystalline compounds having a low viscosity, a small $\Delta n$ and a positive $\Delta \epsilon$. The liquid crystalline compounds referred to herein mean not only compounds exhibiting liquid crystal phases, but also those which usually exhibit no liquid crystal phase, but effectively function in a certain aspect of liquid crystal behavior when they are dissolved in other liquid crystal compounds. Further, among the compounds of the present invention, there are a number of compounds which have a nematic phase in the vicinity of room temperature. Further, the compounds of the present invention are superior in their stability to heat, light, electricity, air, moisture, etc., properties required for liquid crystal materials. Further, the compounds of the present invention are also superior in the compatibility with other liquid crystalline compounds such as those of esters, Schiff base compounds, azoxy compounds, biphenyl compounds, cyclohexane compounds, pyridine compounds, pyrimidine compounds, etc.; hence when the compounds of the present invention are mixed with these compounds or mixtures thereof, it is possible to constitute liquid crystal compositions suitable for various kinds of liquid crystal display elements. For example, when the compounds of the present invention are added as a component of a liquid crystal component to the composition for TN display elements, they have an effectiveness of lowering the $\Delta n$ and viscosity thereof without lowering the NI point and $\Delta \epsilon$ of the liquid crystal composition so much. Furthermore, the compounds of the present invention are superior in practical nematic properties in the vicinity of room temperature as compared with 2-(trans-4-n-alkylcyclohexyl)-5-n-alkylpyrimidines and hence have more excellent characteristics as a component of liquid crystal compositions for liquid crystal display elements of TN type, SBE type, guest-host type or DAP type making use of a nematic phase. For example, 2-(trans-4-pentylcyclohexyl)-5-butylpyrimidine is a liquid crystalline compound having a CN point of 3.5° C. and a monotropic NI point of −7° C., whereas 2-(trans-4-pentylcyclohexyl)-5-butoxypyrimidine as a compound of the present invention is an enantiotropic liquid crystal having a CN point of 33° C. and a NI point of 43° C., that is, it is superior in nematic properties.

The present invention will be described in more detail by way of examples, but it should not be construed to be limited thereto. In examples, crystalline-nematic phase transition point and nematicisotropic phase transition point are abbreviated to CN point and NI point, respectively.

EXAMPLE 1

2-(Trans-4-pentylcyclohexyl)-5-methoxypyrimidine

Trans-4-pentylcyclohexanecarbonitrile (200 g, 1.1 mol), anhydrous ethanol (77 g, 1.7 mol) and toluene (200 ml) were introduced into a reactor purged with nitrogen gas and agitated at −5° C., followed by passing hydrogen chloride gas through the mixture until it was saturated with the gas, further agitating it in a nitrogen current at room temperature for 3 days, adding anhydrous ethanol (2 l) to the reaction mixture, cooling it down to −5° C., then passing ammonia gas therethrough with stirring under cooling until it was saturated with the gas, further agitating the resulting material at room temperature in nitrogen current for 5 days, filtering the reaction mixture and concentrating the filtrate in an evaporator under reduced pressure to obtain trans4-pentylcyclohexanecarboxamidine hydrochloride (239 g, 1.0 mol).

This trans-4-pentylcyclohexanecarboxamidine hydrochloride (69 g, 0.30 mol) and dimethyl methoxymalonate (48 g, 0.30 mol) were added to a solution of sodium methylate (56 g, 1.0 mol) dissolved in anhydrous methanol (1 l), followed by heating the mixture under reflux with stirring for 5 hours, thereafter cooling the resulting material, mixing it with 6N-hydrochloric acid (500 ml), agitating the mixed liquid at room temperature for 20 minutes, filtering the liquid under suction through a filter, washing the resulting residue on the filter with water and methanol and drying it under reduced pressure to obtain 2-(trans-4-pentylcyclohexyl)-4,6-dihydroxy-5-methoxypyrimidine (67 g, 0.23 mol).

To this product (60 g, 0.20 mol) was added phosphorus oxychloride (200 ml), followed by heating the mixture under reflux for 15 hours, distilling off phosphorus oxychloride under reduced pressure, adding toluene (300 ml) to the residue to extract the product, washing the toluene solution three times with 6N-hydrochloric acid (200 ml), then three times with 2N-sodium hydroxide aqueous solution (200 ml) and further with water until the aqueous layer became neutral, drying the toluene solution with anhydrous sodium sulfate, distilling off toluene, recrystallizing the resulting residue from a mixed solvent of ethanol and heptane (1:1) and removing the solvent under reduced pressure to obtain 2-(trans-4-pentylcyclohexyl)-4,6-dichloro-5-methoxypyrimidine (51 g, 0.15 mol) having a melting point of 29.5°~30.4° C.

To this product (50 g, 0.15 mol) were added triethylamine (46 g, 0.45 mol), palladium on carbon (5%) (5.0 g), ethanol (350 ml) and water (35 ml), followed by having hydrogen gas absorbed in the mixture at room temperature until the mixture was saturated with the gas, filtering the reaction material, washing the residue with toluene, concentrating the toluene solution and the filtrate under reduced pressure, subjecting the residue to extraction with toluene (300 ml), washing the toluene solution three times with 2N-NaOH aqueous solution (200 ml) and further with water until the aqueous layer became neutral, then drying the toluene solution with anhydrous sodium sulfate, filtering off the drying agent, subjecting it to vacuum distillation to obtain a fraction (b.p. 155° C./0.5 mmHg) and three times recrystallizing this fraction from ethanol to obtain the objective 2-(trans-4-pentylcyclohexyl)-5-methoxypyrimidine (29 g, 0.11 mol) having a CN point of 20° C. and a NI point of 27° C. Further, the elementary analysis values of this compound accorded well with the theoretical values thereof as follows:

| Element | Observed value | Theoretical value |
| --- | --- | --- |
| C | 73.2% | 73.24% |
| H | 10.0% | 9.99% |
| N | 10.7% | 10.67% |

EXAMPLE 2

KOH (9.5 g, 0.17 mol) and ethylene glycol (100 ml) were added to 2-(trans-4-pentylcyclohexyl)-5-methoxypyrimidine (7.4 g, 0.028 mol) prepared in the same manner as in Example 1, followed by heating the mixture under reflux with stirring for 3 hours, cooling the resulting material, adding glacial acetic acid (30 ml) thereto, further adding water (100 ml), filtering the reaction mixture under suction through a filter, sufficiently washing the residue on the filter with water, three times recrystallizing the residue from ethanol and removing ethanol under reduced pressure to obtain 2-(trans-4-pentylcyclohexyl)-5-hydroxypyrimidine (4.9 g, 0.020 mol) having a melting point of 190.0°~191.1° C.

This product (3.0 g, 0.012 mol) and butyl iodide (6.7 g, 0.036 mol) were added to a solution of sodium methylate (1.0 g, 0.019 mol) dissolved in anhydrous methanol (20 ml), followed by heating the mixture under reflux for 20 hours, concentrating the reaction liquid under reduced pressure, adding toluene (50 ml) to the residue to extract the product, three times washing the resulting toluene solution with 2N-NaOH aqueous solution (50 ml), further washing with water until the aqueous layer became neutral, drying the toluene solution with anhydrous sodium sulfate, distilling off the toluene, three times recrystallizing the residue from heptane and removing the heptane under reduced pressure to obtain the objective 2-(trans-4-pentylcyclohexyl)-5-butoxypyrimidine (2.1 g, 0.0069 mol). This compound had a CN point of 33° C. and a NI point of 43° C. Further, the elementary analysis values of this compound accorded well with the theoretical values thereof as follows:

| Element | Observed value | Theoretical value |
| --- | --- | --- |
| C | 74.9% | 74.95% |
| H | 10.6% | 10.60% |
| N | 9.2% | 9.20% |

EXAMPLES 3~14

Compounds prepared in the same manner as in Example 1 and Example 2 and the values of physical properties thereof are shown in Table 1 together with the results of Example 1 and Example 2.

In the column of phase transition point in Table 1, C represents crystalline phase; N, nematic phase; I, isotropic liquid phase; and ( ), monotropic transition. $\eta_{20}$ represents a viscosity at 20° C. Further, $\Delta n$, $\Delta \epsilon$ and $\eta_{20}$ represent values obtained by extrapolation from the values of physical properties of mixed systems consisting of the compounds of the present invention and a phenylcyclohexane liquid crystal composition. NI points of the mixture systems are also shown.

TABLE 1

| | In formula (I) | | Phase transition point (°C.) | | | | | | NI point |
|---|---|---|---|---|---|---|---|---|---|
| Example | $R_1$ | $R_2$ | C | N | I | $\Delta n$ | $\Delta \epsilon$ | $\eta_{20}$(cP) | (°C.) |
| 1 | n-$C_5H_{11}$ | $CH_3$ | • 20 | • 27 | • | 0.067 | 6.3 | 17.1 | 65.1 |
| 2 | " | n-$C_4H_9$ | • 33 | • 43 | • | 0.047 | 4.3 | 17.8 | 64.4 |
| 3 | " | $C_2H_5$ | • 65 | (• 54) | • | 0.067 | 4.3 | 15.8 | 65.5 |
| 4 | $C_2H_5$ | $CH_3$ | • 23 | | • | 0.013 | 3.6 | 9.8 | 57.9 |
| 5 | " | $C_2H_5$ | • 51 | | • | 0.020 | 2.9 | 3.1 | 57.4 |
| 6 | " | n-$C_3H_7$ | • 30 | | • | 0.012 | 2.8 | 20.7 | 55.8 |
| 7 | " | n-$C_4H_9$ | • 27 | | • | 0.013 | 2.9 | 19.8 | 57.1 |
| 8 | " | n-$C_5H_{11}$ | • 21 | | • | 0.012 | 2.8 | 15.1 | 55.9 |
| 9 | n-$C_3H_7$ | $CH_3$ | • 33 | (• 15) | • | 0.053 | 6.3 | 11.8 | 62.2 |
| 10 | " | $C_2H_5$ | • 76 | | • | 0.053 | 5.6 | 8.5 | 63.3 |
| 11 | " | n-$C_4H_9$ | • 42 | | • | 0.033 | 3.6 | 13.8 | 62.3 |
| 12 | " | n-$C_6H_{13}$ | • 48 | | • | 0.033 | 3.4 | 17.4 | 63.3 |
| 13 | " | n-$C_7H_{15}$ | •57 | (• 44) | • | 0.027 | 2.9 | 18.5 | 62.3 |
| 14 | n-$C_7H_{15}$ | $CH_3$ | • 29 | • 34 | • | 0.027 | 2.9 | 17.8 | 65.6 |

EXAMPLE 15 (Use example)

A liquid crystal composition A consisting of

| | |
|---|---|
| $C_3H_7$—〈H〉—〈O〉—CN | 24 parts by weight |
| $C_5H_{11}$—〈H〉—〈O〉—CN | 36 parts by weight |
| $C_7H_{15}$—〈H〉—〈O〉—CN | 25 parts by weight |
| $C_5H_{11}$—〈H〉—〈O〉—〈O〉—CN | 15 parts by weight | had a NI point of 72.0° C., a viscosity at 20° C. $\eta_{20}$ of 27.8 cP, a $\Delta \epsilon$ of 11.6 ($\epsilon \parallel = 16.1$, $\epsilon \perp = 4.5$) and a $\Delta n$ of 0.140 ($n_e = 1.632$, $n_o = 1.492$). When this composition was filled in a TN cell of 10 μm thick, the cell had a threshold voltage of 1.75 V and a saturation voltage of 2.40 V.

A liquid crystal composition obtained by adding 15 parts by weight of 2-(trans-4-pentylcyclohexyl)-5-methoxypyrimidine as a compound of the present invention to 85 parts by weight of the above liquid crystal composition A had a reduced NI point and $\eta_{20}$ down to 65.1° C. and 26.2 cP, respectively. Further, when this composition was filled in the above TN cell, the threshold voltage and saturation voltage of the resulting cell was reduced to 1.52 V and 2.15 V, respectively.

The present invention provides novel compounds useful as a components of liquid crystal compositions and liquid crystal materials useful for liquid crystal display elements having electrooptical effects applied thereto.

What we claim is:

1. A 2-(trans-4-alkylcyclohexyl)-5-alkoxypyrimidine expressed by the formula (I)

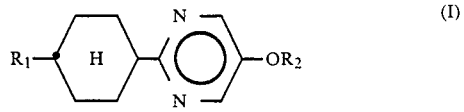

wherein $R_1$ and $R_2$ each independently represent an alkyl group of 1 to 12 carbon atoms.

2. The 2-(Trans-4-alkylcyclohexyl)-5-alkoxypyrimidine according to claim 1 wherein $R_1$ is n-$C_5H_{11}$ and $R_2$ is selected from $CH_3$, $C_2H_5$ and n-$C_4H_9$.

3. The 2-(Trans-4-alkylcyclohexyl)-5-alkoxypyrimidine according to claim 1 wherein $R_1$ is $C_2H_5$ and $R_2$ is selected from $CH_3$, $C_2H_5$, n-$C_3H_7$, n-$C_4H_9$ and n-$C_5H_{11}$.

4. The 2-(Trans-4-alkylcyclohexyl)-5-alkoxypyrimidine according to claim 1 wherein $R_1$ is n-$C_3H_7$ and $R_2$ is selected from $CH_3$, $C_2H_5$, n-$C_4H_9$, n-$C_6H_{13}$ and n-$C_7H_{15}$.

5. The 2-(Trans-4-alkylcyclohexyl)-5-alkoxypyrimidine according to claim 1 wherein $R_1$ is n-$C_7H_{15}$ and $R_2$ is $CH_3$.

6. A liquid crystal composition comprising at least one liquid crystal compound and at least one pyrimidine compound expressed by the formula (I)

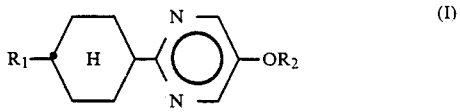

wherein $R_1$ and $R_2$ each independently represent an alkyl group of 1 to 12 carbon atoms.

7. A liquid crystal composition according to claim 6 wherein $R_1$ is n-$C_5H_{11}$ and $R_2$ is selected from $CH_3$, $C_2H_5$ and n-$C_4H_9$.

8. A liquid crystal composition according to claim 6 wherein $R_1$ is $C_2H_5$ and $R_2$ is selected from $CH_3$, $C_2H_5$, n-$C_3H_7$, n-$C_4H_9$ and n-$C_5H_{11}$.

9. A liquid crystal composition according to claim 6 wherein $R_1$ is n-$C_3H_7$ and $R_2$ is selected from $CH_3$, $C_2H_5$, n-$C_4H_9$, n-$C_6H_{13}$ and n-$C_7H_{15}$.

10. A liquid crystal composition according to claim 6 wherein $R_1$ is n-$C_7H_{15}$ and $R_2$ is $CH_3$.

* * * * *